United States Patent [19]
Pies

[11] 3,942,358
[45] Mar. 9, 1976

[54] METHOD AND APPARATUS FOR ADJUSTING DEFECT GATE IN ULTRASONIC PULSE-ECHO TESTING

[75] Inventor: Wilfried Pies, Erftstadt-Bliesheim, Germany

[73] Assignee: Krautkramer-Branson, Incorporated, Stamford, Conn.

[22] Filed: Apr. 29, 1975

[21] Appl. No.: 572,880

[30] Foreign Application Priority Data
May 9, 1974 Germany............................ 2422439

[52] U.S. Cl. ................. 73/67.7; 73/67.8 S; 73/67.9
[51] Int. Cl.² ......................................... G01N 29/04
[58] Field of Search ................ 73/67.8 S, 67.9, 67.7

[56] References Cited
UNITED STATES PATENTS

| | | | |
|---|---|---|---|
| 3,640,122 | 2/1972 | Nusbickel | 73/67.9 |
| 3,646,805 | 3/1972 | Walters | 73/67.9 |

*Primary Examiner*—James J. Gill
*Attorney, Agent, or Firm*—Ervin B. Steinberg; Philip J. Feig

[57] ABSTRACT

The present invention refers to a method of ultrasonic testing a workpiece by the pulse-echo technique and an apparatus therefor. An initial portion of a workpiece to be tested is conveyed past an array of electroacoustic transducer probes. The transit time through the workpiece of the transmitted ultrasonic signals from each probe comprising the array is measured. The maximum measured transit time is stored. Subsequently as a slightly shifted second portion of the workpiece is conveyed past this array of transducers, the transit time through the workpiece of ultrasonic signals transmitted by each probe of the array is again measured. The stored value is updated responsive to the latter obtained values. The final updated value is conducted to a flaw detector circuit for terminating a defect gate used in conjunction with testing the workpiece for defects by the pulse-echo test method.

23 Claims, 5 Drawing Figures

METHOD AND APPARATUS FOR ADJUSTING DEFECT GATE IN ULTRASONIC PULSE-ECHO TESTING

SUMMARY OF THE INVENTION

This invention refers to an ultrasonic test method and more specifically concerns a method for automatically adjusting a defect gate in response to the thickness of a moving workpiece using the pulse transit time method in combination with one or more transmit-receive transducer probes.

It is known to equip production machines with test stations for nondestructively testing workpieces by ultrasonic energy and, most commonly, transmit-receive transducer probes are used which operate in the pulse-echo mode.

Contrasted with manual testing, when using automatic test equipment which forms a part of the production process, it is necessary to automatically adjust the test equipment for the thickness of the particular workpiece under test. During the translating motion of the workpiece through the test station, changing characteristics of the workpiece must be recognized and the automatic equipment must be responsive to the new conditions by effecting a corresponding adjustment of the defect gate in such a manner as to preclude that an unacceptably wide thickness region within the workpiece in proximity to the rear wall remains untested.

In the case of an automated test station adapted for testing flat workpieces, such as plate stock, which are subjected to translating motion by feed means past a test station, a distinction can be made between two sets of adjustments deemed necessary:

1. Adjustments related to the maintenance of the test installation; these are required periodically and are made, therefore, at extended time intervals;
2. Adjustments which are necessary prior to or during the feeding of the workpiece.

The adjustments required under the first-stated set of adjustments can be designed in such a manner that the service interval for the test station is chosen to accomodate the production schedule. The adjustments mentioned under the latter set are a function of the workpiece processing. The mechanical portion and the ultrasonic portion of a test apparatus must be adjusted for the characteristics of the workpiece. Typically, the test apparatus must be set for the width, thickness, length, temperature and translational speed of the workpiece. These parameters either remain constant during the feeding of the workpiece, or the test apparatus must be capable of adjusting itself responsive to changes of the parameters. The mechanical adjustment of a test station for given workpiece parameters and for effecting automatic compensation for changes of such parameters provides no insurmountable problems considering the present state of the art. Compensation can be accomplished substantially automatically and an installation of this type truly can be considered an automatic test system.

The present invention addresses itself to the problem of adjusting the ultrasonic test portion of a test system during feeding of the workpiece as necessitated by changing properties of the workpiece. Compensating, for instance, for the width and length of a workpiece can be accomplished automatically with a mechanically coupled sensing device. Adjustment for the workpiece thickness, however, must be made manually, i.e., the defect gate in the receiver circuit of the ultrasonic test installation must be set prior to the feeding of the workpiece so that the gate is set to the required pulse width corresponding to the thickness of the workpiece region under test. In order to provide automation for this adjustment, an additional thickness measuring station would be necessary. Providing an automated thickness measuring station in advance of the test station, however, entails several difficulties. First, a mechanical arrangement utilizing a workpiece contacting member, in most instances, is not feasible since there will be an excessive amount of mechanical wear, especially when testing hot workpieces. Alternatively, if a noncontacting thickness measurement is made using ultrasonic energy, such an arrangement operates properly only when a defect free workpiece zone is disposed at the thickness measuring location. If erroneous measurements of workpiece thickness due to defects in the workpiece are to be avoided, the system must be capable of providing several measuring probes operating in a spaced parallel relationship and disposed at different locations of the workpiece for measuring the thickness dimension when no defect is present in the workpiece. However, this method fails if a defect is present simultaneously at all of the locations where a measurement is made, i.e. when the defect is so extensive as to affect all of the values measured.

The defect gate must be adjustable responsive to variations in plate thickness, as well as responsive to changes in the transit time of the ultrasonic energy through the test region caused by temperature changes. For example, a temperature increase of 50 degrees C of the transducer probe, the coupling medium and the plate stock causes a change in transit time of approximately five percent. Expressed otherwise, if the defect gate prior to the temperature increase was adjusted to its optimum value, then after the temperature increase has occurred, there remains a region of several millimeters in proximity to the rear surface which remains untested because of the premature closing of the defect gate.

The instant invention concerns a method which obviates the need for a manual adjustment of the ultrasonic test portion of a plate test system during feeding and subsequent translational motion of the workpiece through such station and avoids, moreover, the need for a separate measuring station. Still further, the arrangement disclosed hereafter provides for measurements which are more precise and avoids the generation of erroneous data.

The present arrangement, according to the invention, includes means for establishing during a first time interval, when the workpiece is initially fed into the test station, the time when the ultrasonic energy enters the workpiece entrant surface. This is accomplished, for instance, by known automatic gate positioning means. Furthermore, each transducer probe is sequentially actuated during at least one predetermined time interval and the respective transit times of the ultrasonic pulse signals through the workpiece are determined, preferably in digital form, and the maximum value thereof is stored and used to electronically determine the closing of the defect gate. Hence, the gate width corresponds to the thickness of the workpiece under test. During an ensuing second time interval the maximum value of the transit time for the signal transmitted from each probe is determined and the value newly derived is compared with the maximum value previously stored. If the last derived value differs from the previously stored value, the stored value is updated.

The above described method avoids the occurrence of an undesired nontested thickness region disposed in proximity to the rear wall of the workpiece. Still further, the arrangement described above provides automatic compensation for changes in the transit time of sound energy occurring during the feeding of the workpiece through the test station and such compensation is independent of the cause of the change, as for instance, temperature variation.

A principal object of this invention, therefore, is the provision of a method for generating a signal for terminating a defect gate in an ultrasonic pulse-echo test apparatus.

A further object of the invention is the provision of a method for automatically adjusting a defect gate in a pulse-echo test apparatus to compensate for variations of the workpiece thickness and temperature.

Another salient feature of the invention is the provision of a method for generating a defect gate in a pulse-echo test apparatus, the gate width being minimally affected by defects disposed in the workpiece.

A further object of the invention is the provision of a test arrangement which obviates the heretofore required use of a separate mechanical workpiece thickness measuring station in an ultrasonic pulse-echo test system.

Further and still other objects of the present invention will become more clearly apparent from the description when taken in conjunction with the accompanying drawings.

DETAILED DESCRIPTION OF THE INVENTION

Figure 1:
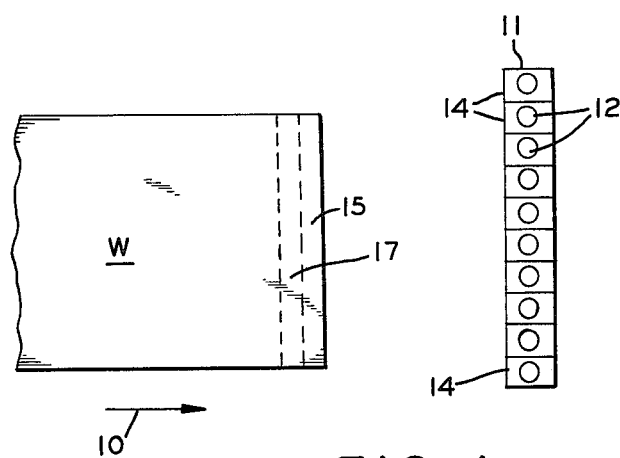
FIG. 1 is a plan view of an arrangement for ultrasonic thickness measuring and pulse-echo defect testing of a workpiece in accordance with the present method.

Referring to FIG. 1, the present invention concerns a system for testing workpieces, particularly metal plate stock. The plate stock W is transported by feed means (not shown) in the direction of arrow 10. A bridge type arm 11 is disposed crosswise to the path of the plate stock and this arm is provided with a plurality of supports 14 each of which supports a respective transmit-receive transducer probe 12. The test pattern is defined by a plurality of parallel longitudinal paths extending along the length of the workpiece. The transducer probes are not energized simultaneously but rather are operated in sequence.

Figure 2:
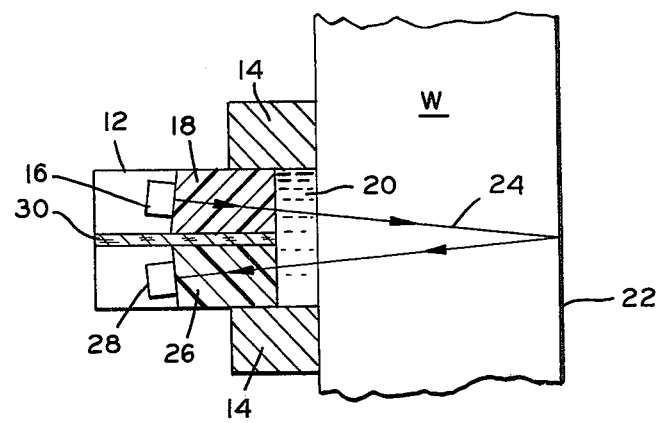
FIG. 2 is a sectional view of a transmit-receive transducer probe coupled to the workpiece.
Figure 3:
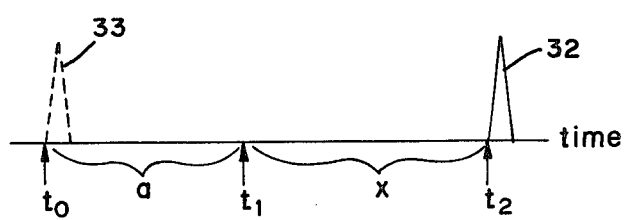
FIG. 3 is a graphical representation of the cathode ray tube screen showing the transmit pulse and the time delayed echo responsive signal.

In FIG. 2, a transmit-receive transducer probe 12, disposed in a respective support 14, is coupled to the workpiece W for transmitting ultrasonic energy into the workpiece and receiving echo signals therefrom. Ultrasonic search pulses are produced by the transmit transducer 16 and are propagated via a coupling member 18 and a water gap 20, serving as a couplant, to the workpiece W. The transmitted ultrasonic pulses, reflected at the rear wall 22 of the workpiece W as shown by the sound beam path 24, traverse the workpiece and pass via the water gap 20 and the coupling member 26 to the receive transducer 28. The transmit and receive transducer halves of the probe are acoustically and electrically decoupled by a sound absorbing barrier layer 30. The pictorial representation as seen on a cathode ray tube screen is shown in FIG. 3 wherein the signal 33 indicates the transmitted signal. The transmitted pulse 33 is not visible since it is produced at the transmit transducer 16 and the cathode ray tube screen indicates normally only the signals received by the receive transducer 28.

The distance $a$ on the cathode ray tube screen is a measure of the transit time of sound from the transmit transducer 16 to the entrant surface of the workpiece (path through delay line), and the distance $x$ is a measure of the thickness of the workpiece W.

The value $a$ is determined for each probe individually prior to the start of the test process and is stored as a digital value since it can be considered constant for each individual test channel during the subsequent test cycle. Updating of this value is necessary only if wear is experienced either at the test probe or at its support. Determination of the value $a$, its storage and recall from storage during testing is performed as will be described hereinafter. The time required for the sonic energy to traverse the workpiece thickness, that is, $t_2 - t_1$ in FIG. 3 has been designated as $x$. The value $x$ is unknown prior to feeding the workpiece into the test station and can be determined by using the circuit shown in the schematic electrical block diagram per FIG. 4.

The distance $a$ of the coupling path of each transducer probe 12 disposed in the array per FIG. 1 is determined by measuring the transit time of the ultrasonic energy search pulse signal 33 to travel from the transmit transducer 16 to the rear surface of a gage block and reflect back to the receive transducer 28. The sound velocity and thickness of the gage block are known. The distance $a$ is obtained by subtracting the known thickness of the gage block from the length of the ultrasonic energy path measured.

In the present embodiment, clock 34 provides the timing and synchronizing signals for the probe array. A ring counter 36 coupled to the clock 34 provides output signals on conductors 38 to a decoder 40 which includes ultrasonic pulse generating means. The decoder is coupled to the respective transmit/receive probes 12 comprising the array. In the present illustration four probes 12 are shown but it shall be understood that the actual number of probes 12 in the array is dependent upon the width of the workpiece W and the scan area of the probes 12. Responsive to the output pulse signals from the decoder 40 each probe 12 sequentially transmits and receives an ultrasonic signal, which signal is reflected at the rear surface of the workpiece. Each probe 12 is coupled to a common receiver 42 which sequentially provides a signal to a preset counter 44 indicative of the rear wall echo signal received by a respective probe 12. It must be understood that in lieu of the multiplexing arrangement of the type shown, in an alternative embodiment, each probe 12 can be associated with a respective pulser/receiver unit.

Figure 4:
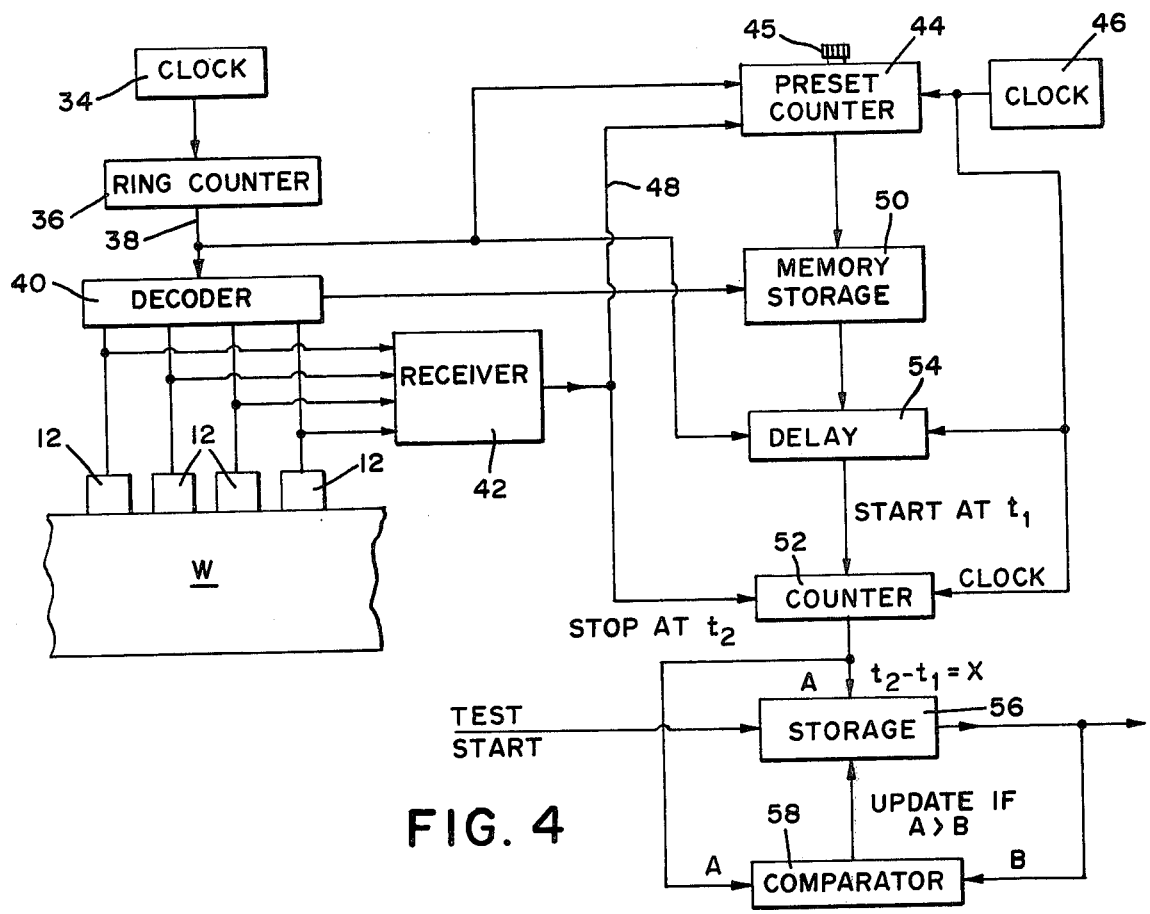
FIG. 4 is a schematic electrical circuit block diagram of a preferred embodiment of an electrical circuit used for measuring the maximum thickness of the workpiece.

An additional clock 46 is provided for causing high frequency pulse signals to be applied to the respective counting elements of the circuit shown in FIG. 4. The ring counter 36 provides a signal to preset counter 44 for causing the preset counter 44 to commence counting at a rate determined by the clock 46 from its preset value (equal to the thickness of the gage block) as manually set by control 45 substantially simultaneously with the transmit pulse 33 being transmitted by the transducer 16. Upon receipt of the preset counter 44 of the received signal along conductor 48, responsive to the receipt of the rear wall responsive echo signal, the counter 44 stops counting. The output of the preset counter 44 is stored in memory storage 50 for each respective probe 12 for later recall and use. A signal from decoder 40 is provided to memory storage 50 to ensure that the count at the output of preset counter 44 is stored in the correct storage in memory storage 50 for the respective probe 12. The value thus stored is the value $a$. This coupling distance is stored and recalled from storage for adjusting the leading edge of the defect gate at the time $t = t_1$, per FIG. 3, when the respective test probe is used for measuring the transit time of the ultrasonic energy through a workpiece. The stored values $a$ corresponding to the coupling path length preferably are in digital form.

Responsive to the workpiece being fed into the test system, a signaling device coupled to the mechanical portion of the system, produces a "Test Start" signal. The Test Start signal zeroizes the test system. That is, the Test Start signal is conducted to storage means 56 and storage means 60 for resetting both the storage means to zero prior to the commencement of the transit time measurements. At this time, the events as described in connection with FIG. 1 begin. Each transducer probe 12 in the array sequentially transmits a transmit pulse signal from transmit transducer 16, which signal traverses the thickness of the workpiece and the signal is received by the receive transducer 28 after being refelected at the rear wall 22. The digital counter 52, FIG. 4, starts to count at the time $t = t_1$, the value $t_1$ being recalled from the memory storage 50. Delay circuit 54 is preset to the value $a$ stored in memory storage 50 for each respective probe. When the signal 33 is transmitted from transducer 16, the delay circuit 54 begins to count at the rate determined by the clock 46. When the delay circuit 54 has counted a number of clock pulses from clock 46 equal to the preset value, an output signal is provided to counter 52, causing the counter 52 to commence counting. It is apparent that the counter 52 has been delayed for a time interval equal to the stored value $a$ or $t_1$. The time $t_1$ is the value $a$ stored as described above. The counter 52 is stopped at the time $t = t_2$ whereby time $t_2$ is determined by the receipt of the first echo signal from receiver 42 after the transmit pulse signal has entered the workpiece. If the workpiece has no defects, the echo signal received is that arising from the rear wall 22. The counter 52 now contains a digital number responsive to the time interval $t_2 - t_1 = x$. This number is stored in a digital storage means 56.

During the following test cycle in which the next transducer probe is operated the same cycle of events repeats, however, the newly derived digital count is stored in storage means 56 only if the newly derived value for $x$ exceeds the previous value of $x$ stored in the storage means 56. The necessary determination is made by the comparator means 58. The comparator 58 compares the stored value B in the storage means 56 with the present value A at the output of counter 52. When the new or present value A representing the distance $x$ is greater than the stored value B, the new value A of the distance $x$ replaces the stored value B. The value A then is compared with the computed thickness $x$ of the subsequent test cycle. After a predetermined quantity of timing cycles, the value of $x$ stored in the storage means 56 represents the true maximum value of the individual transit times of ultrasonic energy through the workpiece obtained from all the probes up to that time.

If defects are discerned in the workpiece and indicated during the time intervals used for determining the maximum transit time, such defects will appear as echo signals in the region between $t_1$ and $t_2$, that is, a value representing $x$ is derived which is not responsive to the actual thickness of the workpiece, but which is less than the value stored in storage means 56. However, it is improbable that a defect of such size is present as to be intercepted by the signals from all of the transducer probes of the array. In that case, it is sufficient that the ultrasonic energy beam 24, from at least one probe be reflected at the rear wall of the workpiece since only the maximum value of $x$ is stored in the storage means 56.

In the event the situation arises when no rear wall echo signal is received and only a defect responsive echo signal is received, it is required that before defect testing of the workpiece commences another thickness measuring station be provided which gauges the distance between the upper surface and lower surface of the workpiece and thereby produces an approximation of the plate thickness. Aside from a mechanical feeler gage, an ultrasonic test system can be used with operates from both sides of the workpiece as is well known in the art. In the absence of a work piece in the measuring gap, the fixed distance between the opposing ultrasonic probes is measured ultrasonically by the through-transmission method. When a plate is interposed in the gap, each probe determines the distance to the closest, respective surface of the plate by the pulse reflection method. The sum of both distances, the distances between the test probes and the facing workpiece surfaces, when subtracted from the total fixed distance between the probes provides a measure of the plate thickness. The value thus derived is used to establish a tolerance range for the values of $x$ produced by the counter 52. Only values of $x$ falling within this tolerance range are accepted and validated for further evaluation.

After a predetermined quantity of test cycles deemed necessary for establishing the maximum value for $x$ has occurred, the first interval for determining the width of the defect gate during the initial feeding of the workpiece in the region 15 is concluded. The resultant maximum value for $x$ is considered to be a first approximation for the actual value of $x$. A signal defining the end of the first time interval is provided along conductor 66 to the storage means 60. The storage means 60, upon receipt of the signal, acquires and stores the maximum value of $x$ stored in storage means 56. The signal along conductor 66 can be derived from a counter which counts a predetermined number of test pulses. Alternatively, the signal can be provided from a switch which is actuated after a predetermined length of the workpiece has passed the thickness measuring station.

Figure 5:
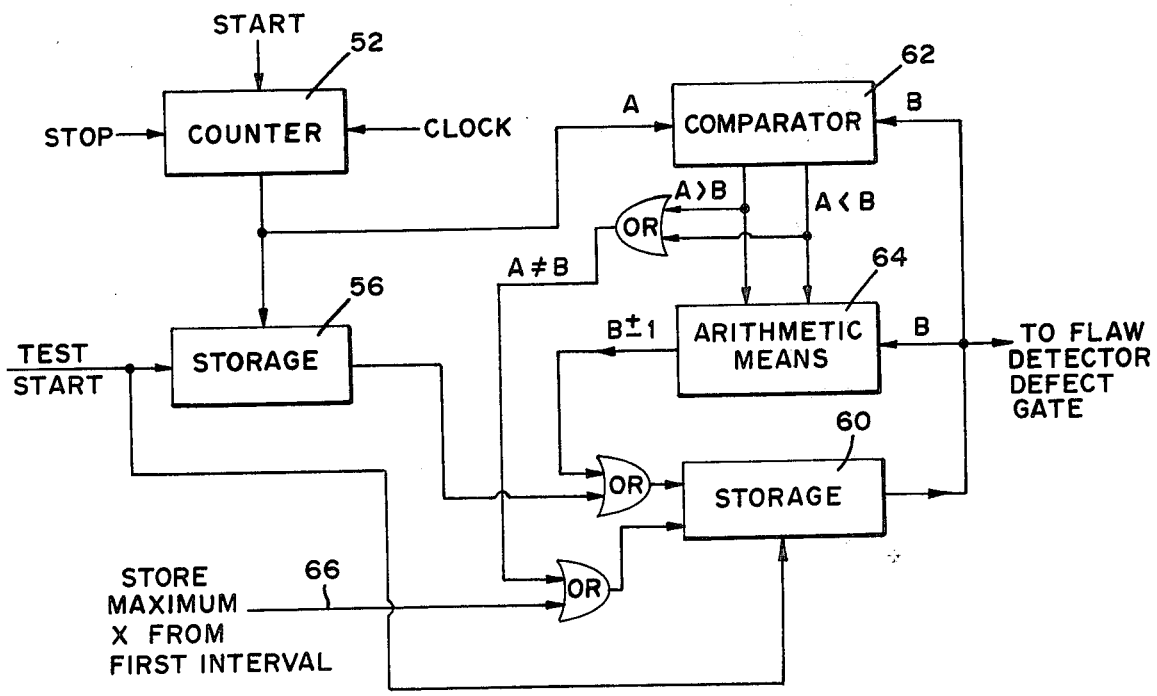
FIG. 5 is a schematic electrical circuit block diagram of an electrical circuit for use in conjunction with the electrical circuit per FIG. 4 for updating the measured thickness value of the workpiece.

In the ensuing second time interval when another workpiece portion, such as the portion 17, passes the transducer array 11, again a predetermined quantity of test cycles is used for deriving the final value for $x$. The necessary signal evaluation is made by means of an electrical circuit shown in FIG. 5. The digital counter 52 counts in the same manner as during the first interval the value $x$ for each test probe. The first value $x$ derived during the second interval is compared with the maximum value $x$ obtained previously during the first interval. At the beginning of the second interval, the maximum value stored in the storage means 56 is transferred to the storage means 60 as stated hereinabove. The comparison means 62 performs the comparison between the previous maximum value B and the newly measured thickness value A. If the value A derived during the second interval is smaller than the maximum value for B obtained during the first interval and stored in storage means 60, the maximum value $x$ then stored in storage means 60, is decreased in the arithmetic means 64 by one count and inserted as a new base value $x$ in the storage means 60. However, if the value $x$ derived during the second interval is larger than the maximum value obtained during the first interval, the first obtained value is increased by a count "one" in the arithmetic unit 64 and such new value $x$ is inserted as a new base value in the storage means 60. Also, if the value $x$ obtained during the second interval equals the maximum value previously obtained, the arithmetic unit 64 is not operated and the maximum value stored in the storage means 60 remains unchanged and is retained as the base value. The same cycle of events occurs for each probe during the second interval. Responsive to the comparison determination between the value stored in the storage means 60 and the value derived during the current or second test interval, the base value for $x$ is either increased by one count, decreased by one count or remains unchanged. After the passage of a sufficiently large quantity of test cycles the value for $x$ appearing at the output of the storage means 60 corresponds to the most likely value of $x$. This value corresponds to the actual wall thickness of the workpiece, provided that it is not affected too often by defect responsive echoes. By limiting the values of $x$ measuring during the second time interval to those values which exceed a predetermined minimum as stated heretofore, the undesired effect caused by receipt of defect responsive echoes affecting the value $x$ can be limited to only those defects which are disposed in close proximity to the rear wall of the workpiece. However, in practice, defects of this kind occur only rarely and, therefore, do not affect the value of $x$ during the second interval and thus do not provide an erroneous measurement for the actual wall thickness of the workpiece. At the conclusion of the second interval, the digital count for $x$ produced and stored in storage means 60 is conducted to a flaw detection device, not shown, for terminating the open state of the defect gate used for inspection of the workpiece by the transducer probes in transducer array 11 during the ensuing defect test interval.

In the flaw detector, the distance $a$ for each probe in the array is measured and stored either in a manner as described above or by using any known method for measuring the value $a$, see German Patent Application OS 23 21 699.1. The defect gate is opened after the time interval $a$ associated with a respective probe in the array has elapsed. The defect gate width is determined by the value $x$ provided from the storage means 60 described hereinabove.

An embodiment for operating the defect gate comprises a clock and a preset counter. The counter initially is preset to the value $x$ derived in the storage means 60. Upon the expiration of the time interval $a$ the defect gate is opened. A signal is provided to the counter to cause the counter to commence counting clock pulses. After a quantity of pulses equal to the preset value are counted, the counter provides a signal for closing the defect gate. For example, the defect gate can be the output from a bistable multivibrator which is triggered by the delay pulse at time $t_1$ and retriggered by the counter after the time interval $x$. It is apparent that while one embodiment for generating a defect gate is described, many variations using the thickness of the workpiece $x$ as a base value may be constructed.

It is also apparent that in an alternative thickness measurement and defect testing arrangement, especially for testing non-uniform workpieces, i.e. wedges or workpieces with irregular contours, each probe in the thickness measurement array 11 is associated with a respective probe in an additional array of probes for providing defect gates of varying duration across the width of the workpiece, which gate durations conform to the thickness of the workpiece region associated with the respective test probe.

Testing of the workpiece for internal defects occurs after the second time interval when the updated value for $x$ is stored in storage means 60. The counter 52 operates at all times and counts during each test pulse the value of $x$. The value of $x$ in storage means 60 is updated as described in connection with the second interval concurrently with the defect testing. Since during the test cycle the defect gate is operative, an erroneous value for $x$ can be considered to be nearly impossible if only those echo signals for updating $x$ are processed which occur later in time than the closing of the defect gate.

Additionally or alternatively, the value of $x$ obtained from counter 52 can be screened and only those values of $x$ which fall within a narrow tolerance range are used for terminating the counting of counter 52. The reference value of the tolerance range is not fixed, rather the prevailing defect gate width can serve as a reference value.

In the event the value $x$ changes by only a small amount between two consecutive test cycles, being caused, for example, by a change in the thickness tolerance of the plate stock along its transverse or longitudinal axis, the value for $x$ is updated for each transmit pulse responsive to the altered condition. That is, the actual count for $x$ established in the preceding test pulse is compared with the adjusted gate width and if necessary is corrected by the addition or subtraction of one count. Therefore, the defect gate width correction is provided for the succeeding defect test pulses occurring across the width of the workpiece.

When testing hot workpieces, heating of the test probes is unavoidable. The heat induced change of the sound velocity in the coupling material 18 and the couplant 20 causes an increase of the pulse transit time and, hence, an increase for the value of $x$. Whereas the updating of the value for $x$ from transmit pulse to transmit pulse is achieved by only one count, it will be apparent that the time taken to compensate the defect gate, considering pulse repetition rates in the kilohertz range, is considerably shorter than is necessitated by the heating of the test probe.

While in the above description the stored count is updated by one count responsive to the counts measured during the second time interval, it will be apparent that the updating can be a predetermined quantity of counts.

For determining whether there is a proper degree of coupling between the probe and workpiece, i.e. whether a correct test was initiated, it is possible to utilize the presence of a control signal in the defect gate and/or in a gate utilized for the rear surface echo observation, which signal indicates "coupling in order" or conversely the absence thereof being indicative of "coupling failure." The defect gate and the gate for the rear surface echo observation should follow each other in close proximity, that is, the rear surface echo gate occurs at the time when the defect gate terminates. Since the defect gate terminates at a time when the ultrasonic energy is at a point in front of and in close proximity to the rear wall, an immediate ensuing rear surface echo gate would occur simultaneously with the receipt of a rear wall responsive echo signal. The simultaneous occurrence of a rear wall responsive echo signal and the rear surface echo gate as measured by a conventional logic gate indicates "coupling in order." The failure to receive a rear wall responsive echo signal during the rear surface echo gate time interval indicates "coupling failure."

While there has been described and illustrated a preferred embodiment of the present invention pertaining to ultrasonic pulseecho testing of workpieces, it will be apparent to those skilled in the art that various changes and modifications can be made without deviating from the broad principle of the invention which is limited only by the scope of the appended claims.

What is claimed is:

1. The method of ultrasonic testing a workpiece by the pulseecho technique comprising:
    determining at first locations of the workpiece the transit time of an ultrasonic signal through the workpiece;
    storing a signal responsive to the longest transit time;
    determining subsequently at second locations of the workpiece the transit time of the ultrasonic signal through the workpiece and producing respective signals responsive to the transit time at said second locations;
    comparing said stored signal with said signals produced at said second locations, and
    updating said stored signal responsive to said signals produced at said second locations.

2. The method of ultrasonic testing as set forth in claim 1, and utilizing the updated stored signal for terminating the defect gate in a flaw detector circuit.

3. The method of ultrasonic testing as set forth in claim 1, said first locations being selected to correspond to an initial portion of the workpiece.

4. The method of ultrasonic testing as set forth in claim 3, said second locations being disposed adjacent to the first locations of the workpiece.

5. The method of ultrasonic testing as set forth in claim 1, said respective transit times at said first locations and second locations being determined sequentially.

6. The method of ultrasonic testing as set forth in claim 5, updating comprising increasing the stored signal by a predetermined amount if a respective signal responsive to the transit time at a second location is greater, decreasing the stored signal by a predetermined amount if a respective signal responsive to the transit time at a second location is smaller, or leaving the stored signal unchanged if a respective signal responsive to the transit time at a second location is substantially identical with said stored signal.

7. The method of ultrasonic testing a workpiece by the pulse-echo technique comprising:
    providing a plurality of spaced transducer probes for transmitting ultrasonic energy into the workpiece in a direction across its thickness;
    coupling respectively first surface locations of the workpiece to said probes;
    energizing sequentially said probes for causing each probe to send an ultrasonic search pulse into the workpiece at a respective such location and to receive an echo signal arising from a change in acoustic impedance sensed by said pulse;
    producing for each of said locations a signal responsive to the transit time of the associated search pulse from the surface of the workpiece to the change in acoustic impedance;
    comparing said signals and storing a digital signal corresponding to the longest transit time;
    coupling subsequently respective second locations of the workpiece to said probes;
    energizing sequentially said probes for causing each probe to send an ultrasonic search pulse into the workpiece at a respective such second location and receive an echo signal arising from a change in an acoustic impedance sensed by said search pulse;
    producing for each of said second locations a signal responsive to the transit time of the associated search pulse from the surface of the workpiece to the change in acoustic impedance;
    updating the stored digital signal in dependence upon the transit time responsive signals produced at said second locations by comparing said last stated signals with the stored signal and changing the stored signal by predetermined increments or decrements, and
    utilizing the updated stored signal for terminating the defect gate in a flaw detector circuit.

8. The method of ultrasonic testing as set forth in claim 7, said respective signals responsive to said transit times being digital values.

9. The method of ultrasonic testing as set forth in claim 7, said plurality of transducer probes forming an array, and providing relative motion between the workpiece and said array for coupling during a first time interval said first locations to said probes and during a subsequent second time interval said second locations to said probes.

10. The method of ultrasonic testing as set forth in claim 9, said workpiece being plate stock and providing relative motion comprising subjecting said plate stock to translating motion relative to said array of probes disposed transverse to the direction of said translating motion.

11. An ultrasonic pulse echo test apparatus comprising:
    electroacoustic transmit-receive transducer probes disposed in an array for transmitting ultrasonic pulse signals into a workpiece and receiving echo signals therefrom;
    electrical means coupled to each of said probes for energizing each probe sequentially during a first and a second time interval and for receiving echo responsive signals from each of said probes;

counting means coupled to said electrical means for providing counts commensurate with the transmit time of the ultrasonic pulse signal from a respective probe traveling from the entrant surface to an ultrasonic energy reflecting surface in the workpiece;

first selection and storage means coupled to said counting means for selecting and storing the maximum value of said counts provided during the first time interval;

second storage means coupled to said first selection and storage means and said counting means for receiving said stored maximum value of said counts at the beginning of said second interval and updating said stored maximum value responsive to said counts produced during the second time interval for providing an updated count, and means coupled to said second storage means for providing said updated count to a flaw detector for terminating an open defect gate.

12. An alternate pulse echo test apparatus as set forth in claim 11, said first selection and storage means including comparison means for comparing the value stored with the count at the output of said counting means and for causing said first storage means to store the larger count for obtaining a maximum value.

13. An ultrasonic pulse echo test apparatus as set forth in claim 12, said second storage means including comparison means for comparing the value stored in said second storage means with each count at the output of said counting means and providing a signal indicative of which signal is larger.

14. An ultrasonic pulse echo test apparatus as set forth in claim 13, said second storage means further including an arithmetic means coupled to said comparison means for causing said stored value in said second storage means to be increased by a predetermined count when said signal from said comparison means indicates that the value stored is smaller than the count at the output of said counting means, or for causing said stored value to be decreased by a predetermined count when said signal from said comparison means indicates that the value stored is larger than the count at the output of said counting means, and causing said stored value to remain unchanged when said signal from said comparison means indicates that the value stored is substantially equal to the count at the output of said counting means.

15. A pulse echo test apparatus as set forth in claim 14, said counting means including means providing an output count only when said count exceeds a predetermined value.

16. An ultrasonic pulse echo test apparatus comprising:

electroacoustic transmit-receive transducer probes each including delay means disposed in an array coupled to a workpiece for transmitting ultrasonic pulse signals into a workpiece and receiving echo signals therefrom;

electrical means coupled to each of said probes for energizing each probe sequentially during a first and a second time interval and for receiving echo responsive signals from each of said probes;

counting means coupled to said electrical means for providing counts commensurate with the transit time of the ultrasonic pulse signal from a respective probe traveling from the entrant surface to an ultrasonic energy reflecting surface of the workpiece;

first selection and storage means coupled to said counting means for selecting and storing the maximum value of said counts provided during the first time interval;

second storage means coupled to said first selection and storage means and said counting means for receiving said stored maximum value of said counts at the beginning of said second interval and updating said stored maximum value responsive to said counts produced during the second time interval for providing an updated count, and means coupled to said second storage means for providing said updated count to a flaw detector for terminating an open defect gate.

17. An ultrasonic pulse echo test apparatus as set forth in claim 16, and inhibit means coupled to said counting means for delaying the start of the count until the pulse signal has entered the workpiece.

18. An ultrasonic pulse echo test apparatus as set forth in claim 16, said first selection and storage means including comparison means for comparing the value stored with the count at the output of said counting means and for causing said first storage means to store the larger count for obtaining a maximum value.

19. An ultrasonic pulse echo test apparatus as set forth in claim 18, said second storage means including comparison means for comparing the value stored in said second storage means with each count at the output of said counting means and providing a signal indicative of which signal is larger.

20. An ultrasonic pulse echo test apparatus as set forth in claim 19, said second storage means further including an arithmetic means coupled to said comparison means for causing said stored value in said second storage means to be increased by a predetermined count when said signal from said comparison means indicates that the value stored is smaller than the count at the output of said counting means, or for causing said stored value to be decreased by a predetermined count when said signal from said comparison means indicates that the value stored is larger than the count at the output of said counting means, and causing said stored value to remain unchanged when said signal from said comparison means indicates that the value stored is substantially equal to the count in the output of said counting means.

21. A pulse echo test apparatus as set forth in claim 20, said counting means including means providing an output count only when said count exceeds a predetermined value.

22. An ultrasonic pulse echo test apparatus comprising:

electroacoustic transmit-receive transducer probes each including delay means disposed in an array and disposed for transmitting ultrasonic pulse signals into a workpiece and receiving echo signals therefrom;

electrical means coupled to each of said probes for energizing each probe sequentially during a first and during a second time interval and for receiving echo responsive signals from each of said probes;

first means coupled to said electrical means for obtaining for each probe a respective delay count commensurate with the transit time of the ultrasonic pulse signal through the associated delay means;

storage means coupled to said first means for storing said delay count associated with a respective probe in the array;

counting means coupled to said electrical means for providing a thickness count for each probe commensurate with the transmit time of the ultrasonic pulse signal from a respective probe through the associated delay means to an echo signal producing ultrasonic energy reflecting surface in the workpiece;

second means coupled to said counting means and said storage means for subtracting from a respective thickness count in said counting means a count commensurate with said delay count stored for the associated probe;

comparison means coupled to said counting means for determining the maximum of said thickness counts during the first time interval;

additional storage means coupled to said comparison means for storing the maximum of said thickness counts at the end of the first time interval;

additional comparison means coupled to said additional storage means and to said counting means for comparing the stored count in said additional storage means with the thickness counts of said counting means derived during said second time interval and providing an output signal responsive to such comparison;

third means coupled to said additional comparison means and to said additional storage means for causing said stored count in said additional storage means to be updated responsive to said output signal, and fourth means coupled to said additional storage means for providing said updated count to a flaw detector circuit for terminating an open defect gate.

23. An ultrasonic pulse echo test apparatus comprising:

a plurality of electroacoustic transmit-receive transducer probes disposed in an array for transmitting ultrasonic pulse signals into a workpiece and receiving echo signal therefrom;

electrical means coupled to each of said probes for energizing each probe sequentially during a first and a subsequent second time interval and for receiving echo responsive signals from said probes;

timing means coupled to said electrical means for providing for each probe transit time responsive signals of the associated pulse signal traveling from the entrant surface of the workpiece to an ultrasonic energy reflecting surface;

first selection and storage means coupled to said timing means for selecting and storing a signal responsive to the longest transit time provided during said first interval;

second storage means coupled to said first selection and storage means and said timing means for receiving said signal responsive to the longest transit time and updating said last-mentioned signal sequentially responsive to the transit time responsive signals produced during the second time interval whereby to provide an updated stored signal in said second storage means, and means coupled to said second storage means for providing said updated signal to a flaw detector for terminating an open defect gate.

* * * * *